United States Patent [19]

Beck et al.

[11] 4,125,723
[45] Nov. 14, 1978

[54] PROCESS FOR THE PREPARATION OF TETRACHLOROPYRIMIDINE

[75] Inventors: Gunther Beck; Helmut Heitzer, both of Leverkusen, Germany

[73] Assignee: Bayer Aktiengesellschaft, Leverkusen, Germany

[21] Appl. No.: 851,309

[22] Filed: Nov. 14, 1977

[30] Foreign Application Priority Data

Nov. 25, 1976 [DE] Fed. Rep. of Germany ....... 2653616

[51] Int. Cl.² ............................................. C07D 239/24
[52] U.S. Cl. .................................................. 544/334
[58] Field of Search .................................... 260/251 R

[56] References Cited

U.S. PATENT DOCUMENTS

| | | | |
|---|---|---|---|
| 3,714,164 | 1/1973 | Steffan | 260/251 R |
| 3,997,554 | 12/1976 | Van Eyck et al. | 260/251 R |
| 4,026,892 | 5/1977 | Beck et al. | 260/251 R |

Primary Examiner—Nicholas S. Rizzo
Attorney, Agent, or Firm—Plumley and Tyner

[57] ABSTRACT

Process for the preparation of tetrachloropyrimidine, characterized in that compounds of the formula

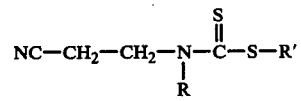

wherein
R = a radical which can be split off under the reaction conditions and
R' = optionally substituted lower allyl radical, are reacted with chlorine or agents which release chlorine, preferably at temperatures from 0° to 150° C and using more than 7.5 mols of chlorine, preferably 8 to 9 mols of chlorine.

7 Claims, No Drawings

PROCESS FOR THE PREPARATION OF TETRACHLOROPYRIMIDINE

The present invention relates to a new process for the preparation of tetrachloropyrimidine.

The process is characterised in that (2-cyanoethyl)-dithiocarbamic acid esters of the formula

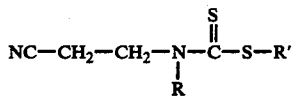

wherein
R denotes a radical which can be split off under the reaction conditions and
R' denotes an optionally substituted lower alkyl radical, are reacted with chlorine or compounds which release chlorine, if appropriate mixed with an inert diluent. The reaction is carried out, for example, at temperatures from 0°–150° C. with more than 7.5 mols of chlorine, preferably 8 to 9 mols of chlorine, and especially 9 mols of chlorine.

In a preferred embodiment, the chlorination is carried out at temperatures from about 40° C. to about 70° C. until the evolution of HCl has virtually ended and the mixture is then further heated to temperatures from 70° to 130° C. A further preferred embodiment consists in carrying out the chlorination at temperatures from about 40° to 130° C.

Suitable radicals R which can be split off under the reaction conditions are, in particular, lower alkyl, preferably $C_1$–$C_4$-alkyl, such as methyl, ethyl, propyl or butyl, and furthermore, lower alkenyl, especially $C_2$–$C_4$-alkenyl, such as allyl, it being possible for these groups also to be substituted, for example by chlorine, $C_1$–$C_4$-alkoxy or optionally substituted phenyl.

Suitable radicals of this type are, for example, chloroethyl, methoxyethyl, benzyl, phenylethyl, chloropropyl, dichloropropyl and methoxypropyl.

Methyl is particularly preferred.

Suitable optionally substituted lower alkyl radicals R' are, preferably, $C_1$–$C_4$-alkyl, such as methyl, ethyl, propyl and butyl, it being possible for these groups also to be substituted, for example by chlorine, $C_1$–$C_4$-alkoxy or optionally substituted phenyl.

Suitable radicals of this type are, for example, chloroethyl, methoxyethyl, benzyl and phenethyl.

Methyl is particularly preferred.

In addition to chlorine, all the customary chlorinating agents which can split off chlorine under the reaction conditions are, of course, suitable.

Examples which may be mentioned are: sulphur dichloride, sulphuryl chloride and phosphorus pentachloride.

Although the starting compounds of the formula (I) are not known, they can be easily prepared according to the instructions in the literature for the preparation of dialkyldithiocaramic acid alkyl esters (for example J. Chem. Soc. 1944, page 151) by initially reacting, according to the following equation

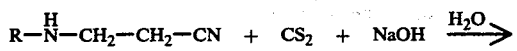

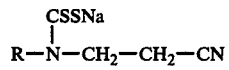

cyanoethylated amines (II), in which R has the meaning given above, with carbon disulphide in aqueous sodium hydroxide solution to give the dithiocarbamates of the formula (III), which are then converted, by alkylation, into the esters of the formula (I), for example with (substituted) alkyl halides, sulphonic acid alkyl esters or dialkyl sulphates, for example with dimethyl sulphate, according to the following equation:

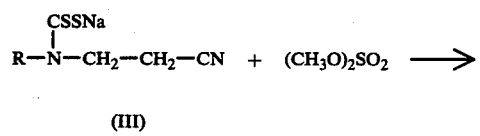

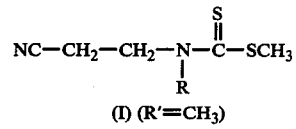

The cyanoethylated amines (II) are obtained, for example, according to the following equation

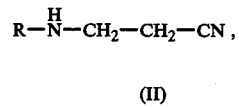

by subjecting primary amines (IV), in which R has the abovementioned meaning, to an addition reaction with acrylonitrile; (compare, for example, J. Am. Chem Soc. 66, 725 (1944); J. Am Chem. Soc. 68, 1217 (1946); J. Am. Chem. Soc. 78, 2573 (1956); and J. Heterocyclic Chem. 1, 260 (1964).

(2-Cyanoethyl)-dithiocarbamic acid esters of the formula (I) which are suitable for the process according to the invention are, for example: (2-cyanoethyl)-methyl-dithiocarbamic acid methyl ester, (2-cyanoethyl)-ethyl-dithiocarbamic acid methyl ester, (2-cyanoethyl)-methyl-dithiocarbamic acid ethyl ester, (2-cyanoethyl)-ethyl-dithiocarbamic acid ethyl ester, (2-cyanoethyl)-methyl-dithiocarbamic acid propyl ester, (2-cyanoethyl)-methyl-dithiocarbamic acid butyl ester, (2-cyanoethyl)-methyl-dithiocarbamic acid chloroethyl ester, (2-cyanoethyl)-butyl-dithiocarbamic acid benzyl ester, (2-cyanoethyl)-butyl-dithiocarbamic acid methyl ester, (2-cyanoethyl)-benzyldithiocarbamic acid methyl ester and (2-cyanoethyl)-benzyl-dithiocarbamic acid benzyl ester.

Diluents which are inert under the reaction conditions are all sovents which are stable towards chlorine, for example chlorinated aliphatic and aromatic hydrocarbons, such as methylene chloride, chloroform, carbon tetrachloride, 1,1,2,2-tetrachloroethane, tetrachloroethylene, 1,1,2,3,3-pentachloropropane, hexachlorocyclopentadiene, octachlorocyclopentene and 1,2,4-trichlorobenzene, chlorinated pyrimidines and phosphorus oxychloride. In general, 0.5 to 20, preferably 1 to 10, parts by volume of diluent are used per part by weight of (I).

In the case where the chlorinating agent is a liquid under the reaction conditions, such as, for example, sulphur dichloride or sulphuryl chloride, the additional use of an inert diluent can be omitted.

If chlorine is used as the chlorinating agent, the reaction initially proceeds strongly exothermically. Thus, it is appropriate - especially when larger batches are used - not to carry out the chlorination with an excess of chlorine until the exothermic reaction has subsided. After the strongly exothermic first chlorination phase has subsided, the chlorination is appropriately carried out with an excess of chlorine (recognisable by the greenish colour of the chlorination off-gas) in order to end the reaction as rapidly as possible.

If other chlorinating agents are used, for example $SCl_2$, it can be appropriate to employ an excess from the beginning.

In detail, the process is carried out by initially mixing a (2-cyanoethyl-dithiocarbamic acid ester of the formula (I), especially (2-cyanoethyl)-methyl-dithiocarbamic acid methyl ester, with one of the diluents mentioned, for example chloroform, at room temperature and then adding the chlorinating agent. External cooling and metering of the chlorinating agent are matched with one another so that the initially strongly exothermic reaction does not become too violent.

Chlorination is preferably carried out at about 40° to 70° C. until the evolution of HCl has virtually ended.

If the chlorination is carried out in the absence of an inert diluent using a chlorinating agent which is liquid under the reaction conditions, such as, for example, sulphur dichloride, it is advisable initially to introduce the latter and to meter in the starting material (I) in portions at a temperature at which it reacts with the chlorinating agent as rapidly as possible, that is to say, for example, between 40° and 70° C., preferably 50° and 60° C.

A particularly favourable embodiment of the process consists in initially carrying out the chlorination at about 40° to 70° C. until the evolution of HCl has virtually ended and then heating the mixture to temperatures up to about 100° C., and in particular appropriately until the evolution of HCl, which starts again, has virtually ended.

Tetrachloropyrimidine is suitable as a reactive component for the preparation of reactive dyestuffs (compare, for example, Belgian Patent Specification No. 578,933).

EXAMPLE 50 g (0.288 mol) of (2-cyanoethyl)-methyl-dithiocarbamic acid methyl ester are dissolved in about 250 ml of chloroform in a 0.5 l three-necked flask which is provided with a thermometer, gas inlet tube, stirrer and reflux condenser. A vigorous stream of chlorine is passed in, whilst stirring, the initially strongly exothermic reaction being kept at a temperature between 40° and 50° C. by cooling with ice. After this first stage, which is the most strongly exothermic, has subsided, the stream of chlorine is reduced so that chlorine is always present in a slight excess (recognisable, for example, by the light green colour of the off-gas). The mixture is then subsequently heated for the first time, a reflux temperature of about 59° C. being reached after about 1 hour from the start of chlorination, whilst passing in a further slight excess of a stream of chlorine. The reflux condenser is now replaced by a distillation device and sulphur dichloride and chloroform are distilled off in the slight stream of chlorine until the internal temperature reaches about 100° C. (reached after about 1¾ hours from the start of chlorination).

The residue, which contains tetrachloropyrimidine is distilled in a waterpump vacuum almost quantitatively, until the temperature at which it passes over reaches 110° C./12 mm Hg. According to analysis by gas chromatography, the distillate contains 60 g (corresponding to 95.5% of theory) of tetrachloropyrimidine, which can be obtained pure by fractional distillation at a boiling point 12 of 108° to 110° C.

The starting material, that is to say (2-cyanoethyl)-methyl-dithiocarbamic acid methyl ester, was obtained as follows:

Initially 420 g (5.0 mols) of 3-methylamino-propionitrile and then, in the course of about 10 minutes, 400 g (5.26 mols) of carbon disulphide are allowed to flow into a solution, cooled to 5° C., of 203 g (5.07 mols) of sodium hydroxide in 1,800 ml of water, whilst cooling externally with ice/water. The mixture is then subsequently stirred vigorously for about 1.5 hours, whilst cooling further in an ice bath, a virtually homogeneous phase being formed. 650 g (5.16 mols) of dimethyl sulphate are now added dropwise to the mixture, whilst cooling further with ice, at such a rate that the reaction temperature does not exceed about 30° C. Thereafter, the oily layer which separates out is washed thoroughly with water, after which it solidifies to a colourless crystalline mass of pure (2-cyanoethyl)-methyl-dithiocarbamic acid methyl ester. The melting point, after filtering off and drying, is 45° to 46° C. The compound exhibits a characteristic IR spectrum having the following bands (in $cm^{-1}$): 2,250, 1,490, 1,425, 1,380, 1,300, 1,250, 1,195, 1,100, 1,030, 985, 955 and 755.

We claim:
1. A process for the preparation of tetrachloropyrimidine in which a (2-cyanoethyl)-dithiocarbamic ester of the formula

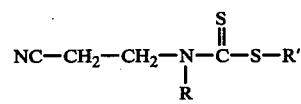

wherein
R is a radical which splits off under the reaction conditions; and
R' is $C_1$-$C_4$-alkyl; or $C_1$-$C_4$-alkyl substituted by chlorine, $C_1$-$C_4$-alkoxy or phenyl; is reacted at a temperature of 0° to 150° C. with chlorine or an agent which releases chlorine under the reaction conditions, in which the amount of chlorine is more than 7.5 mols per mol of said (2-cyanoethyl)-dithiocarbamic acid ester.

2. The process of claim 1 which is conducted at a temperature of 40° to 130° C.

3. The process of claim 1 in which chlorination is conducted at 40° C. to 70° C. until the evolution of HCl has ended and then heating the mixture to 70° C. to 130° C.

4. The process of claim 3 in which heating at 70° C. to 130° C. is conducted in the presence of chlorine.

5. The process of claim 1 in which

R is $C_1$–$C_4$-alkyl; $C_1$–$C_4$-alkyl substituted by chlorine, $C_1$–$C_4$-alkoxy or phenyl; $C_2$–$C_4$-alkenyl; or $C_2$–$C_4$-alkenyl substituted by chlorine, $C_1$–$C_4$-alkoxy or phenyl;

R′ is $C_1$–$C_4$-alkyl; or $C_1$–$C_4$-alkyl substituted by chlorine, $C_1$–$C_4$-alkoxy or phenyl; and said agent which releases chlorine is sulfur dichloride, sulfuryl chloride or phosphorus pentachloride.

6. The process of claim 1 in which R and R′ are $C_1$–$C_4$-alkyl.

7. The process of claim 1 in which R and R′ are methyl.